United States Patent
Chen et al.

(10) Patent No.: US 9,222,141 B2
(45) Date of Patent: Dec. 29, 2015

(54) USE OF BROWN MIDRIB-3 GENE SPECIFIC MARKERS IN MAIZE FOR TRAIT INTROGRESSION

(75) Inventors: Wei Chen, Carmel, IN (US); Nathan J. VanOpdorp, Geneseo, IL (US); Siva P. Kumpatla, Carmel, IN (US); Chandra-Shekara A. Channabasavaradhya, Carmel, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 1205 days.

(21) Appl. No.: 13/105,659

(22) Filed: May 11, 2011

(65) Prior Publication Data

US 2011/0283427 A1 Nov. 17, 2011

Related U.S. Application Data

(60) Provisional application No. 61/334,073, filed on May 12, 2010.

(51) Int. Cl.
*C12Q 1/68* (2006.01)

(52) U.S. Cl.
CPC ........ *C12Q 1/6895* (2013.01); *C12Q 2600/156* (2013.01)

(58) Field of Classification Search
None
See application file for complete search history.

(56) References Cited

U.S. PATENT DOCUMENTS

2010/0071092 A1 3/2010 Carter et al.

FOREIGN PATENT DOCUMENTS

WO 2009111263 A1 9/2009

OTHER PUBLICATIONS

Piquemal et al., Plant Physiology, (2002), vol. 130, pp. 1675-1685.*
Molecular Breeding 3: pp. 351-357, 1997.*
Current Protocols in Human Genetics pp. 2.10.1-2.10.8, 2008.*
Morrow S. L., et al., "Molecular characterization of a brown midrib3 deletion mutation in maize," Molecular Breeding, 1997, pp. 351-357, vol. 3.
Vignois, Florence et al., "The brown midrib3 (bm3) mutation in maize occurs in the gene encoding caffeic acid o-methyltransferase," The Plant Cell, Apr. 1995, pp. 407-416, vol. 7.
Piquemal et al. "Down regulation of Caffeic Acid O-Methyltransferace in Maize revisited Using a Transgenic Approach", Plant Physiology, 2002, pp. 1675-1685, vol. 130.
Guillet-Claude et al., "Genetic diversity associated with variation in silage corn digestibility for three O-methyltransferase genes involved in lignin biosynthesis" Theor Appl. Genet, 2004, pp. 126-135, vol. 110.
He et al., "Improvement of forage quality by down regulation of maize O-methyltransferase", Crop Sci. 2003, pp. 2240-2251, vol. 43.
Kuc et al., "Degradation of Abnormal Lignins in the Brown-midrib mutants and double mutants of maize," 1968 Phytochemistry, pp. 1435-1436, vol. 7.
Fontaine, A.-S. and Barriere, Y. "Taffeic acid 0-methyltransferase allieic polymorphism characterization and analysis in different maize inbred lines." Molecular Breeding, Jan. 2003, vol. 11, pp. 69-75.
Battisini, E. and Noli, Enrico. "Real-time quantification of wild-type contaminants in glycophosphate tolerant soybean," BMC Biotechnology, Mar. 6, 2009, vol. 9, Issue 16.
Chiu, R. W. K. et al. "Determination of RhD zygosity: comparison of a double amplification refractory mutation system approach and a multiplexreal-time quantitative PCR approach," Clinical Chemistry, Apr. 2001, vol. 47, No. 4, pp. 667-672.
International Search Report and Written Opinion for International Application No. PCT/US2011/036118, dated Jan. 9, 2012.
Livak K.J., "Allelic discrimination using fluorgenic probves and the 5' nucleaseassay," Genetic Analysis: Biomolecular Engineering, Jan. 1, 1999. pp. 143-149, vol. 14.
Lester Hui et al., "Genotyping Using the Taqman Assay," Current Protocols in Juman Geneetics, Jan. 1, 2008.

* cited by examiner

*Primary Examiner* — David T Fox
*Assistant Examiner* — Jared Shapiro
(74) *Attorney, Agent, or Firm* — Eric J. Kraus; TraskBritt, P.C.

(57) ABSTRACT

This disclosure concerns compositions and methods for determining the zygosity of corn plants containing one or more brown midrib (BMR) mutations. The disclosure also concerns methods that are useful for enhancing the breeding process for BMR corn. In certain embodiments, compositions and methods for determining the zygosity of corn plants with respect to the bm3 allele.

9 Claims, 10 Drawing Sheets

```
bm3  SEQ ID NO 10    TACTGGCTGCGGCTAGCACAAGGCTGGAAATAGTTATTATCT--------ACGATATAATA 53
COMT SEQ ID NO 11    TACTGGCTGCGGCTAGCACAAGGCTGGAAATAGTTGTTACTTGTTATACACGATATAATA 60
                     *********************************  *   *    ********** bm3  SEQ ID NO 10    TTTCCCTAGAACAAAAAAGTTTTTTTATAAAAAGCAAGAAAGAAAGAAGGAAAGAAAGT 113
COMT SEQ ID NO 11    TTTCTCTAGAACAAAAAAGATTTTTTTTTTATAA------AAAGCAAGCAAGAAAGAAAGT 115
                     ** **********  ***** * *        * * ********** bm3  SEQ ID NO 10    GAGTGACTTCAAGTTTTTCCTAAAAAAAAAGTTAGGAGTGGGATGGAAAAGTCAGCAAGG 173
COMT SEQ ID NO 11    GAGTGACTTCATGTTTTTCCTAAAAAAAA-GTTAGGAGTGGGATGGAAAAGTCAGCAAGG 174
                     *********  ************* ************************** bm3  SEQ ID NO 10    ACCACTTGTTTGTTGTCCACTATCCATCCAGTGGGTGAGACTTTTTTGCGAGACGGAGCA 233
COMT SEQ ID NO 11    ACCACTTGTTTGTTGTCCACTATCCATCCAGTGGGTGAGACTTTTTTGCGAGACGGAGCA 234
                     ************************************************************ bm3  SEQ ID NO 10    CTATATTATTGGCCGACTCCTTTTTCTGTATCCGCAAAACGGCAGCCGTCGATCGCCGGA 293
COMT SEQ ID NO 11    CTATATTATTGGCCGAGTCCCTTTTCTGTATCCGCAAAACGGCAGCCGTCGATCGCCGGA 294
                     ************** * *************************************** bm3  SEQ ID NO 10    CGGATCG-ACGGCTCACATGAGTGTCGAGTCCAATTCCAACCACGAGGGCTGGAAGGAAA 352
COMT SEQ ID NO 11    CGGATCGCACGGCGACACTCAGTGTCGAGTCCAATTCCAACCACGAGCGGCTGCAAGGAAA 354
                     *****    *   ************************* * * ***** bm3  SEQ ID NO 10    ACCATCCGTGCTGGTCTGGACTTTTTGCCAAACTCCATTCAGCCATTCGCCGACTGAAGG 412
COMT SEQ ID NO 11    GCCATCCGTCCTGGTCTGGACTTTTTGCCAAACTCCATTCAGACGTTCGCCCGACTGAAGG 414
                      ******  **************************** *  ***** ****** bm3  SEQ ID NO 10    TGAATCTTCAGACA--GCCAGATTGGTTGGTGTCTAGTGTGTCCGAAGATGGCGTAGAAA 470
COMT SEQ ID NO 11    TGAATCTTCAGACACAGCCAGATTGTTTGGTGTC---------TGCGAAGATGGCGTAGAAA 467
                     ************  ****  ******         * **************** bm3  SEQ ID NO 10    AGACTGAGAGACAGTTGGCTCACACAGACAATTGACAACTGACTATAGTATCTGCCTGCC 530
COMT SEQ ID NO 11    AGACCAAGAGACAGTTGGCTCACACAGACAAGTGACAACTGACTATAGTATCTGCCTGCC 527
                     **  *********************  ************************ bm3  SEQ ID NO 10    TGGCTGATGCTGATAGAGATGGGGACTCTTGTCCTG-CTGTCTGTTCT---------TGTAT 582
COMT SEQ ID NO 11    TGGCTGATGCTGATAGAGATAG---ACTCTTGCCCTGTCTGTTCCTTGTACAAACGTGGAC 585
                     ********************  *  ***** *    * *      ** * bm3  SEQ ID NO 10    AAAT-----------------------------------------CTCCGTTGTCAAATATTT 604
COMT SEQ ID NO 11    AAACATTAGTAGCAGTTTTCTTTGATCTACAAAAAGTACTACCTCAGTTTTTAAATATTT 645
                     *                                          * *** * ******** bm3  SEQ ID NO 10    ATCGTCCGATTATTTATTTYTAAACT-AAACAACGACAAATAAAAAAGAACGAGGTTGCA 663
COMT SEQ ID NO 11    ATCGGCTGTTAGTTTATTTTTGAACTTAAACGACT----------------GGTTGCA 687
                     ****  *  * ******* * **** * ** *                 ******* bm3  SEQ ID NO 10    AAAGATAGATACA-----AACCAAGGA--------------------------- 686
COMT SEQ ID NO 11    AAAGATAGATAGATACAAACGAAAGGATGTCGTCGCTGTGCGCTGATCTGATCACTGCCA 747
                     ***********  *     *  **** bm3  SEQ ID NO 10    ~ 978 bases deletion in bm3 mutant            -----------
COMT SEQ ID NO 11                                                  GGTACTATCT 765 bm3  SEQ ID NO 10    ------------------------------------------------------------
COMT SEQ ID NO 11    CAAGGACGCGGTGCTGGACGGCGGCATCCCGTTCAACAAGGCGTACGGGATGACGGCGTT 825 bm3  SEQ ID NO 10    ------------------------------------------------------------
COMT SEQ ID NO 11    CGAGTACCACGGCACGGACGCGCGCTTCAACCGCGTGTTCAACGAGGGCATGAAGAACCA 885
```

Fig. 3

```
bm3  SEQ ID NO 10   ------------------------------------------------------------
COMT SEQ ID NO 11   CTCGGTGATCATCACCAAGAAGCTGCTGGACTTCTACACGGGCTTCGAGGGCGTGTCGAC 945 bm3  SEQ ID NO 10   ------------------------------------------------------------
COMT SEQ ID NO 11   GCTGGTGGACGTGGGCGGCGGCGTGGGCGCCACGCTGCACGCCATCACGTCCCGCCACCC 1005 bm3  SEQ ID NO 10   ------------------------------------------------------------
COMT SEQ ID NO 11   GCACATCTCCGGGGTCAACTTCGACCTGCCGCACGTCATCTCCGAGGCGCCGCCGTTCCC 1065 bm3  SEQ ID NO 10   ------------------------------------------------------------
COMT SEQ ID NO 11   CGGCGTGCGCCACGTGGGCGGGGACATGTTCGCGTCCGTGCCCGCCGGCGACGCCATCCT 1125 bm3  SEQ ID NO 10   ------------------------------------------------------------
COMT SEQ ID NO 11   CATGAAGTGGATCCTCCACGACTGGAGCGACGCGCACTGCGCCACGCTGCTCAAGAACTG 1185 bm3  SEQ ID NO 10   ------------------------------------------------------------
COMT SEQ ID NO 11   CTACGACGCGCTGCCGGAAAATGGCAAGGTCATCGTCGTCGAGTGCGTGCTGCCGGTCAA 1245 bm3  SEQ ID NO 10   ------------------------------------------------------------
COMT SEQ ID NO 11   CACGGAGGCCACCCCCAAGGCGCAGGGCGTGTTCCACGTCGACATGATCATGCTCGCGCA 1305 bm3  SEQ ID NO 10   ------------------------------------------------------------
COMT SEQ ID NO 11   CAACCCCGGCGGCAAGGAGCGGTACGAGCGCGAGTTCCGCGAGCTCGCCAAGGGCGCCGG 1365 bm3  SEQ ID NO 10   ------------------------------------------------------------
COMT SEQ ID NO 11   CTTCTCCGGGTTCAAGGCCACCTACATCTACGCCAACGCCTGGGCCATCGAGTTCATCAA 1425 bm3  SEQ ID NO 10   ------------------------------------------------------------
COMT SEQ ID NO 11   GTGAATACGGCTACCACCGTCGCCGCGATGAGATGCATGGCTGCCACATGCATGCTTGCT 1485 bm3  SEQ ID NO 10   ------------------------------------------------------------
COMT SEQ ID NO 11   TGCTTGGTCCTCGTATCGTACGTCGCCGTCGTCGTCTTCTTCTGGTTGCGCTGCTACCTT 1545 bm3  SEQ ID NO 10   ------------------------------------------------------------
COMT SEQ ID NO 11   GCTGCTCTCGCCCTCGCGTATGCATGTACTTTTGCTTAATTTTCTTTCTTCATATCATGC 1605 bm3  SEQ ID NO 10   ---------------------------------------------------------TGTC 690
COMT SEQ ID NO 11   ACTCTGGCTGGCCTAGACTGCCCCCGATCCATGGTGGCCATGTCTTCGGTACGTCTTGTC 1665
                                                                             **** bm3  SEQ ID NO 10   CAGCTCTTGCATGTCGTGGAATTCTAAATTCTTCTTCTGCCTCGAATTGTCTCTGCCATGT 750
COMT SEQ ID NO 11   GAGCTCTTGCATGTCGTGGATTCTAAATTCTTCTTCTGCCTCGAATTGTCTCTGCCATGT 1725
                     ********** *** *********************************** bm3  SEQ ID NO 10   GCGAGTAATAACAATCAAGGTTATACTTACCATACAATTACATGGTGGTTTAATTGCTCT 810
COMT SEQ ID NO 11   GCGAGTAATAACAATCAAGGTTATACTTACCATACAATTACATGGTGGTTTAATTGCTCT 1785
                    ************************************************************ bm3  SEQ ID NO 10   CTTTTAATTTGGTGA 825
COMT SEQ ID NO 11   CTTTTAATTTGGTGA 1800
                    ***************
```

Fig. 3 cont.

USE OF BROWN MIDRIB-3 GENE SPECIFIC MARKERS IN MAIZE FOR TRAIT INTROGRESSION

CROSS-REFERENCE TO RELATED APPLICATION

This application claims the benefit of U.S. Provisional Patent Application Ser. No. 61/334,073, filed May 12, 2010, the disclosure of which is hereby incorporated herein in its entirety by this reference.

FIELD OF THE DISCLOSURE

The present disclosure relates generally to plant breeding. Methods are provided for determining the zygosity of plants containing brown midrib 3 (bm3) mutations. Methods of the disclosure are further useful for enhancing the breeding process for BMR-containing plant lines.

BACKGROUND

Lignins are universal components in plants that form cross-links with carbohydrates, such as hemicelluloses in the cell wall. Lignin polymers lower fiber digestion in ruminants, and the degree of lignifications may be inversely proportional to forage crop digestibility. Cherney et al. (1991) Adv. Agron. 46:157-98. Maize containing a brown midrib (BMR) mutation exhibit a reddish brown pigmentation of the leaf midrib that is associated with significantly reduced lignin content, altered lignin composition, and improved digestibility. At least four independent BMR mutations have been identified in maize. Kuc et al. (1968) Phytochemistry 7:1435-6. These mutations, termed "bm1, bm2, bm3, and bm4," all exhibit decreased lignin content when compared to control corn. bm3 mutations include insertions (bm3-1), deletions (bm3-2), and insertion/deletions (bm3-3) within the caffeic acid O-methyltransferase (COMT, e.g., GenBank Accession No. M73235) gene. Morrow et al. (1997) Mol. Breeding. 3:351-7; Vignols et al. (1995) Plant Cell 7:407-16.

The COMT gene controls enzyme activities involved in lignin biosynthesis. COMT utilizes S-adenylsylmethionine to transmethylate caffeic acid, which results in the production of ferulic acid. Coniferyl alcohol and sinapyl alcohol are ultimately generated from the ferulic acid. The combination of coniferyl, ferulic, and sinapyl alcohols in the presence of free radicals results in lignin production. Bm3 mutations have been characterized, and are thought to inhibit the transmethylation of caffeic acid by gene inactivation. Guillet-Claude et al. (2004) Theor. Appl. Genet. 110:126-35; Piquemal et al. (2002) Plant Physiology 130:1-11; He et al. (2003) Crop Sci. 43:2240-51; Morrow et al. (1997) Mol. Breeding. 3:351-7; Vignols et al. (1995) Plant Cell 7:407-16. However, a rapid method for specifically detecting and testing the zygosity of a particular plant at the bm3 locus has not been developed.

SUMMARY OF THE DISCLOSURE

Disclosed herein are methods for high-throughput PCR-based molecular characterization of BMR corn varieties (e.g., bm3 mutants) that may greatly enhance the breeding process for BMR containing lines. Disclosed are methods for determining the zygosity of a plant tissue sample, and hence the plant from which the sample was prepared, by determining the presence or absence of a bm3 mutant and the wild-type COMT alleles. Thus, an endpoint hydrolysis probe PCR-based zygosity assay (which is referenced as a TaqMan® assay herein) is provided that specifically detects and tests the zygosity status at the bm3 locus. Disclosed are assays that utilize a biplex of oligonucleotides specific to a bm3 mutant and to corresponding wild-type sequences in the same assay.

BRIEF DESCRIPTION OF THE FIGURES

FIG. 3 includes an alignment of consensus sequences from bm3 mutants and wild-type COMT genes. Three previously described deletion/insertion mutations are underlined.

SEQUENCE LISTING

Figure 1:
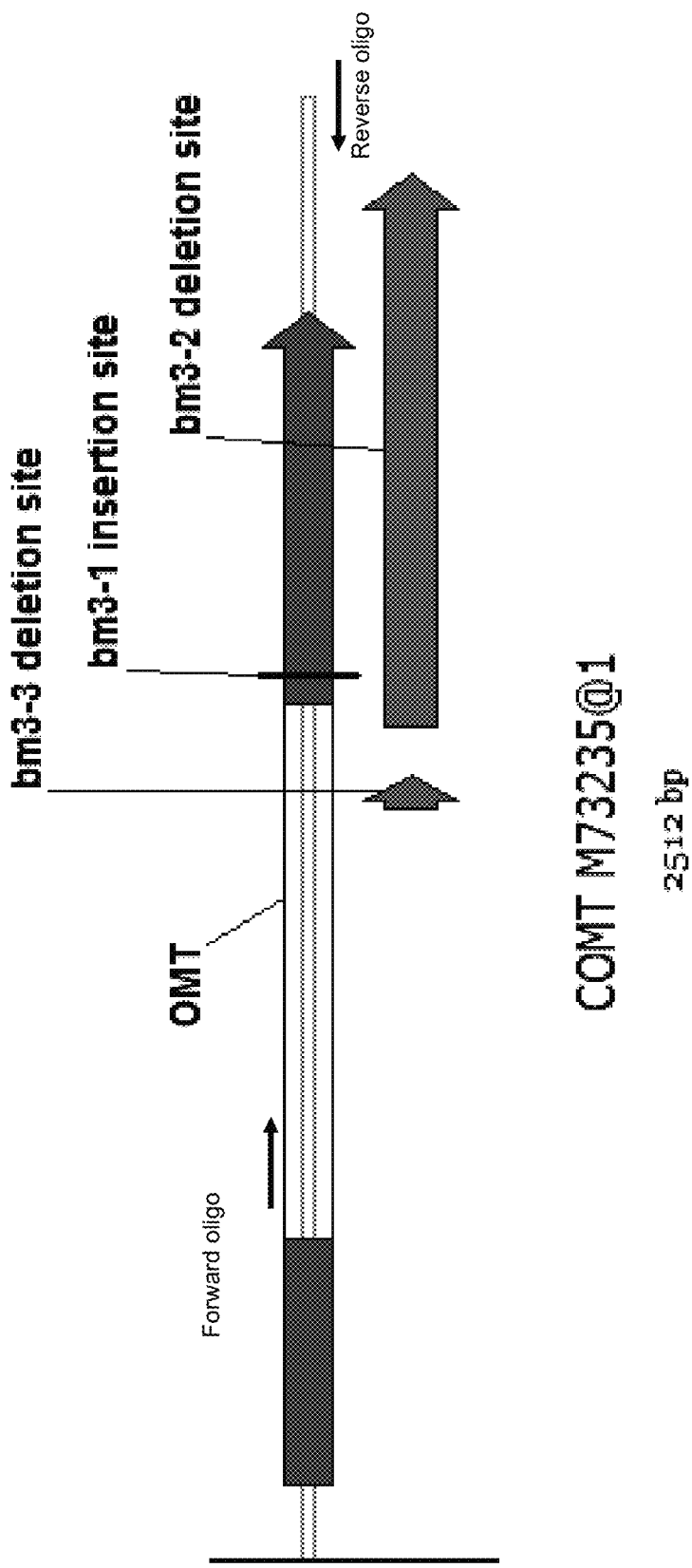
FIG. 1 includes a schematic representation of COMT gene with bm3 mutations and oligonucleotides designed for partial amplification of COMT gene (~1.8 kbp).

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood as included by any reference to the displayed strand. In the accompanying sequence listing:

SEQ ID NO:1 shows a forward primer sequence (BM35_F) used to amplify a corn COMT partial gene: TACTCTACTGGCTGCGGCTAGC.

SEQ ID NO:2 shows a reverse primer sequence (BM35_R) used to amplify a corn COMT partial gene: TAACCTTGATTGTTATTACTCGCACATGG.

SEQ ID NO:3 shows an oligonucleotide sequence (BM1234R) from the COMT gene used to sequence a corn COMT partial gene: ATCAGCATCAGCCAGGCAGG.

SEQ ID NO:4 shows a forward primer sequence (BM3_F) used to identify the mutant bm3 allele: AAAAAGAACGAGGTTGCAAAAGATA.

SEQ ID NO:5 shows a reverse primer sequence (BM3_R) used to identify the mutant bm3 allele: TTAGAATCCACGACATGCAAGAG.

SEQ ID NO:6 shows a probe sequence (BM3_Probe) used to identify the mutant bm3 allele, with FAM at the 5' end, and MGBNFQ at the 3' end: FAM-ACAAACCAAAGGATGTCG-MGBNFQ.

SEQ ID NO:7 shows a forward primer sequence (COMT_F) used to identify the wild-type COMT allele: CGCACTCGACGACGATGAC.

SEQ ID NO:8 shows a reverse primer sequence (COMT_R) used to identify the wild-type COMT allele: CACGCTGCTCAAGAACTGCTA.

SEQ ID NO:9 shows a probe sequence (COMT_Probe) used to identify the wild-type COMT allele, with VIC at the 5' end, and MGBNFQ at the 3' end: VIC-CATTTTCCGGCAGCGC-MGBNFQ.

SEQ ID NO:10 shows a bm3 nucleotide sequence.

SEQ ID NO:11 shows a partial COMT nucleotide sequence.

DETAILED DESCRIPTION

I. Overview of Several Embodiments

Disclosed herein are methods for high-throughput PCR-based molecular characterization of bm3 corn varieties that may greatly enhance the breeding process for BMR containing plant lines. In particular embodiments, the method may comprise obtaining a sample of isolated genomic DNA from a corn plant, contacting the isolated genomic DNA with at least one nucleic acid molecule comprising a nucleotide sequence capable of hybridizing to SEQ ID NO:10 under high stringency conditions and at least one nucleic acid molecule comprising a nucleotide sequence capable of hybridizing to SEQ ID NO:11 under high stringency conditions, and determining the zygosity of a bm3 mutation in the isolated genomic DNA from the corn plant. In particular embodiments, at least one nucleic acid molecule comprising a nucleotide sequence capable of hybridizing to SEQ ID NO:10 under high stringency conditions and at least one nucleic acid molecule comprising a nucleotide sequence capable of hybridizing to SEQ ID NO:11 under high stringency conditions are between 10 and 35 nucleotides in length. In some embodiments, at least one nucleic acid molecule comprising a nucleotide sequence capable of hybridizing to SEQ ID NO:10 under high stringency conditions is at least 95% identical to between 10 and 35 contiguous nucleotides of SEQ ID NO:10. In some embodiments, at least one nucleic acid molecule comprising a nucleotide sequence capable of hybridizing to SEQ ID NO:11 under high stringency conditions is at least 95% identical to between 10 and 35 contiguous nucleotides of SEQ ID NO:11. In some embodiments, a nucleotide sequence capable of hybridizing to SEQ ID NO:11 under high stringency conditions is not capable of hybridizing to SEQ ID NO:10 under high stringency conditions. In certain embodiments, at least one nucleic acid molecule comprising a nucleotide sequence capable of hybridizing to SEQ ID NO:10 or SEQ ID NO:11 is selected from the group consisting of SEQ ID NOs:1-9.

Also disclosed are methods for identifying a BMR mutation in corn plants. In some embodiments, the method may comprise exposing genomic DNA from a corn plant to a nucleic acid molecule capable of hybridizing to SEQ ID NO:10 under high stringency conditions. In particular embodiments, a nucleic acid molecule capable of hybridizing to SEQ ID NO:10 under high stringency conditions may be selected from the group consisting of SEQ ID NO:4, SEQ ID NO:5, and SEQ ID NO:6.

Further disclosed are methods for reliably and predictably introgressing a trait for low lignin content (e.g., through introgression of a bm3 allele) into plant germplasm. In some embodiments, the method may comprise backcrossing a plant having a mutation in the COMT gene with another plant, obtaining a sample of isolated genomic DNA from a progeny plant produced by the cross, contacting the sample of isolated genomic DNA with at least one nucleic acid molecule comprising a nucleotide sequence capable of hybridizing to SEQ ID NO:11 under high stringency conditions, and selecting progeny from the cross that comprise a mutation in the COMT gene by reproducing a plant from which a sample of isolated genomic DNA was obtained that binds with high stringency to at least one nucleic acid molecule comprising a nucleotide sequence capable of hybridizing to SEQ ID NO:11 under high stringency conditions, thereby producing a genetically engineered plant wherein a trait for low lignin content has been introgressed into the germplasm of the genetically engineered plant.

Also disclosed are corn plants with genotype and/or zygosity determined according to high-throughput PCR-based molecular methods of the disclosure, as well as genetically engineered corn plants exhibiting a trait for low lignin content that are produced according to methods of the disclosure for reliably and predictably introgressing a trait for low lignin content into corn plant germplasm.

II. Abbreviations

BMR brown midrib
MGBNFQ Minor Grove Binding Non Flourescence Quencher™ I
FAM 6-carboxy-fluorescein
PCR polymerase chain reaction
RFU relative fluorescence units
VIC 6-carboxy-rhodamine

III. Terms

In the description and tables, which follow, a number of terms are used. In order to provide a clear and consistent understanding of the specification and claims, including the scope to be given such terms, the following definitions are provided:

Backcrossing. Backcrossing is a process in which a breeder repeatedly crosses hybrid progeny back to one of the parents, for example, a first generation hybrid $F_1$ with one of the parental genotypes of the $F_1$ hybrid.

BMR corn: As used herein, the term "BMR corn" refers to corn varieties that contain a brown midrib mutation, such as the mutations characterized as bm1, bm2, bm3, and bm4. BMR corn varieties typically exhibit a reddish brown pigmentation of the leaf midrib. BMR corn is also typically characterized by lower lignin content, higher fiber digestibility, and higher dry matter intake. Non-limiting examples of BMR corn varieties include F2F297, F2F383, F2F488, F2F449, F2F566, F2F610, F2F622, F2F665, F2F633, F2F682, F2F721, F2F700, and F2F797.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the $Na^+$ and/or $Mg^{2+}$ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual*, 2nd ed., vol. 1-3, Cold Spring Harbor Laboratory Press, Cold Spring Harbor, N.Y., 1989, chs. 9 and 11.

For purposes of the present disclosure, "stringent conditions" encompass conditions under which hybridization will occur if there is less than 25% mismatch between the hybridization molecule and the target sequence. "Stringent conditions" can be further defined into particular levels of stringency. Thus, as used herein, "moderate stringency" conditions are those under which molecules with more than 25% mismatch will not hybridize. Conditions of "medium stringency" are those under which molecules with more than 15% mismatch will not hybridize, and conditions of "high stringency" are those under which sequence with more than 10% mismatch will not hybridize. Conditions of "very high stringency" are those under which sequences with more than 6% mismatch will not hybridize.

In particular embodiments, stringent conditions can include hybridization at 60° C. in TaqMan® genotyping master mix (Applied Biosystems, Foster City, Calif., Catalog #4371355), diluted according to the manufacturer's instructions.

Isolated: An "isolated" biological component (such as a nucleic acid or protein) has been substantially separated, produced apart from, or purified away from other biological components in the cell of the organism in which the component naturally occurs, i.e., other chromosomal and extra-chromosomal DNA and RNA, and proteins. Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

Zygosity: As used herein, the term "zygosity" refers to the similarity, or lack thereof, of alleles of a gene for an inherited trait in an organism. If both alleles are the same, the organism is "homozygous" for the trait. If both alleles are different, the organism is "heterozygous" for that trait. If one allele is missing, it is "hemizygous." If both alleles are missing, it is "nullizygous."

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8).

IV. High-Throughput Method for Genotype and Zygosity Determinations of BMR Corn

A. Overview

Described herein is a gene specific end-point TaqMan® PCR assay, generally useful for zygosity analysis of BMR corn or putative BMR corn. Particular examples utilize a biplex of oligonucleotides specific to a bm3 deletion, and to the corresponding wild-type sequences in the same assay. In these examples, zygosity may be determined by the presence/absence of the bm3 mutant and the wild-type COMT alleles. The assay has been submitted to high-throughput genomic analysis group for further implementation and may greatly enhance the breeding process for BMR introgression projects.

B. Brown midrib Corn

Brown midrib (BMR) corn plants are characterized by brown pigmentation in the leaf midrib at the V4 to V6 stage and a light brown coloration of the pith after tasselling. Brown midrib hybrid corn contains a gene mutation that causes lower lignin content in corn plant tissue, for example, a bm2 mutation, or a bm3 mutation. The brown midrib3 gene is located on the short arm of chromosome 4, and the bm3 allele is recessive. The brown midrib2 gene is located on the long arm of chromosome 1, and the bm2 allele is also recessive. Lignin polymers limit the digestibility of the fiber in the corn plant. The reduced lignin in brown midrib corn results in silage with fiber that is more digestible than normal corn. Animal feeding trials have shown about 10 percent greater intake and increased milk production with BMR corn silage, as compared to normal silage.

Methods are provided that identify bm3 mutations. Methods of the disclosure may be useful, for example, in the identification of a particular corn plant, or particular corn variety, as BMR corn. Disclosed methods may also be useful in the reliable and predictable introgression of a BMR trait into corn germplasm by crossing BMR corn with other corn varieties, or by crossing BMR corn containing a first BMR mutation with BMR corn containing a second BMR mutation (for example, crossing a bm1 corn variety with a bm3 corn variety). Many BMR mutations are known to those of skill in the art, and some BMR mutations have been characterized (e.g., mapped and sequenced). Methods of the disclosure may be used to identify a BMR mutation, determine the genotype and/or zygosity of a BMR corn plant or variety, and for the introgression of any BMR mutation into corn germplasm.

C. End-Point PCR Detection Assay

Described herein is a gene specific end-point TaqMan® PCR assay, generally useful for zygosity analysis of BMR corn or putative BMR corn. In particular embodiments, a gene specific end-point TaqMan® PCR assay may be used to analyze the zygosity of corn for a bm3 mutation.

Primers and probes for use in a gene specific end-point TaqMan® PCR assay may be designed based on a known mutation in the gene of interest. For example, primers and probes for a bm3-specific assay may be designed based on a 978 bp deletion at the 3' end of the caffeic acid O-methyltransferase (COMT) gene. In biplex reactions, wherein oligonucleotides specific to the mutation (e.g., bm3) and the undisrupted wild-type gene (e.g., COMT) are used in the same assay, the specific oligonucleotides will selectively amplify sequence from either or both of the mutated gene and/or the wild-type gene that is present in a genomic DNA sample.

In some embodiments, a bm3-specific assay amplifies a fragment that is 71 bp in length, which is unique to the junction site where 978 bp of nucleotide sequence was deleted from the wild-type COMT gene. In certain embodiments, a target-specific oligonucleotide probe (e.g., BM3_Probe (SEQ ID NO:6)) hybridizes under high stringency conditions to a target sequence in a genomic DNA sample between two PCR primers (e.g., BM3_F (SEQ ID NO:4), and BM3_R (SEQ ID NO:5)).

In some embodiments, a wild-type COMT gene-specific assay amplifies a fragment of the COMT gene that is 65 bp in length and which is located within exon 2 (deleted in bm3 mutants), such that non-bm3 sequences at the COMT locus may not be amplified. In certain embodiments, a target-specific oligonucleotide probe (e.g., COMT_Probe (SEQ ID NO:9)) hybridizes under high stringency conditions to a target sequence in a genomic DNA sample between two PCR primers (e.g., COMT_F (SEQ ID NO:7), and COMT_R (SEQ ID NO:8)).

Target-specific oligonucleotides may be labeled, for example, with fluorescent dyes (e.g., FAM, VIC, and MGB-NFQ), which may allow rapid quantification of a target-specific fluorescent signal. PCR products may be measured after a pre-determined number of cycles, for example, when the reaction is in the early exponential phase. Negative control samples may comprise genomic DNA from any corn variety, for example, without a bm3 mutation. Positive control samples may comprise genomic DNA from a corn variety with a BMR mutation, such as a bm3 deletion mutation in the COMT gene. Control hemizygous samples may comprise either genomic DNA from a corn variety predetermined to be hemizygous for a bm3 mutation; or a hemizygous sample may comprise equal proportions of negative control DNA to DNA from a corn variety predetermined to be homozygous for a bm3.

DNA may be isolated (for example, extracted, and purified) from corn plant tissue by methods known to those of skill in the art. Commercial kits for DNA isolation are available, for example, from Qiagen, Inc. In some embodiments, leaf discs from a particular plant are punched and transferred into collection tubes. The puncher may be cleaned after each sampling with 70% alcohol, rinsing in water, and drying. DNA extraction buffers may be prepared according to the manufacturer's recommendations. DNA may then be isolated using the kit according to the manufacturer's instructions. Finally, the concentration of the isolated DNA may be determined using, for example, a Quant-iT™ PicoGreen® Quantification Kit (Invitrogen, Carlsbad, Calif.) and a spectrophotometer, or by any other suitable technique.

Once primers, probes, and genomic DNA sample(s) have been prepared or otherwise made available, a PCR reaction may be conducted to identify nucleic acid sequences of interest (e.g., sequences particular to a BMR mutation) in the genomic DNA sample(s). In particular embodiments, individual PCR reaction mixtures are prepared that contain all the reaction components, except the genomic DNA sample(s). For a biplex reaction comprising primers and gene-specific probes for bm3 mutant and wild-type COMT corn, the reaction mixture may comprise enzyme, reaction buffer, forward and reverse primers for the bm3 mutation, forward and reverse primers for the wild-type COMT gene, a gene-specific probe for the bm3 mutation, a gene-specific probe for the COMT gene, and water. In some PCR assay systems (e.g., TaqMan® PCR assays), enzyme and buffer may be present in a single kit component (e.g., TaqMan® genotyping master mix; Applied Biosystems, Foster City, Calif., Catalog #4371355).

Once the reaction mixture is otherwise prepared, genomic DNA sample(s) may be added, and the reaction commenced. It is not necessary to normalize the amounts of genomic DNA in a sample. However, the skilled artisan may attain best results by using genomic DNA samples with relatively equal concentrations.

In some embodiments, a PCR assay (e.g., a TaqMan® PCR assay) can be set up with appropriate controls. For example, a reaction in a multi-well plate may be performed with control wells comprising: (1) negative control(s) with reagents but no DNA sample; (2) homozygous positive control(s) comprising bm3 corn genomic DNA; (3) and hemizygous positive control(s), as described above. DNA is then amplified by PCR under suitable cycle conditions. For example, in some embodiments using a GenAmp® PCR System 9700, there may be a single initial denaturation cycle at 95° C. for 15 minutes, followed by 30 cycles of denaturation (92° C. for 15 seconds) and annealing/extension (60° C. for 60 seconds). Those of skill in the art understand that PCR cycle conditions may be varied according to the practitioner's discretion, and comparable results obtained.

D. Determination of Genotype and/or Zygosity

A PCR assay (e.g., an end-point TaqMan® PCR assay) may be used for genotype and/or zygosity analysis of BMR corn or putative BMR corn. In some embodiments, a gene-specific oligonucleotide probe may be labeled with a reporter (e.g., a fluorescent moiety). For assays using fluorometric detection, PCR reaction products may be analyzed in a spectrofluorometer (e.g., Tecan GENios™; Männedorf, Switzerland) using excitation and emission wavelength settings appropriate for the detection of the probe(s). For example, the fluorescent dye, FAM, may be measured with an excitation wavelength of 485 nm, and an emission wavelength of 535 nm. Alternatively, the fluorescent dye, VIC, may be measured with an excitation wavelength of 525 nm, and an emission wavelength of 560 nm.

Following the completion of the PCR reaction and probe detection, a table and distribution graph may be generated using, for example, any suitable computer graphics software. Results obtained with wild-type, hemizygous, and homozygous DNA of similar genotypic background may serve as negative and positive controls. In a segregating population, three clusters of data points may be obtained allowing the visual determination of a sample result as likely belonging to one of the segregated clusters. Alternatively, data analysis computer software may be used to calculate the probability that a sample result belongs to each segregated cluster, with the most probable cluster serving as the sample designation. When a visual determination is made, the boundary of each cluster may be arbitrary, for example, when three clusters of data points are clearly visible.

Raw fluorescence intensity data may also be analyzed directly from a plate reader using a suitable analysis package, such as KLIMS (KBioscience laboratory information management system). A graph with the relative fluorescence units (RFU) of a fluorescence signal generated by a specific probe for a mutant allele plotted on one axis, and the RFU of a fluorescence signal generated by a specific probe for the wild-type allele plotted on the other axis may be generated. Zygosity determinations may then be made based on the cluster separation in a graphical display of the data.

Samples that do not contain mutant genomic DNA (e.g., a BMR mutation) may only result in fluorescence readings of the wild-type PCR product. Samples containing hemizygous or homozygous mutant genomic DNA may result in RFU readings for the mutant-specific probe higher than that of a negative background control. If a sample yields no adequate results, the genomic DNA in the sample may not be of adequate quality and/or quantity, and a new DNA preparation and/or new PCR reaction should be performed. Preferably, a negative control sample containing no DNA sample shows very low detection of gene-specific probe(s). It is also preferable that known homozygous controls show only high detection of the mutant or wild-type DNA in the control, and that known hemizygous controls show both high detection of the mutant and wild-type DNA.

A "test run" of the PCR method and genotype and/or zygosity determination may be performed with all appropriate controls prior to screening of samples. Further optimization of the methods may be desirable for components that may differ among uses (e.g., method of genomic DNA preparation, Taq DNA polymerase, oligonucleotides, laboratory equipment, etc.). PCR and thermal cycling conditions may be established that amplify both mutant and/or wild-type sequences in a known genomic DNA template with acceptable levels of probe detection (e.g., acceptable RFU for fluorescently labeled oligonucleotide probes).

E. Introgression of a Trait for Low Lignin Content into Plant Germplasm

Described herein are methods for producing a corn plant with low lignin content (e.g., BMR corn), through conventional plant breeding involving sexual reproduction. Methods may comprise crossing a first parent corn plant that comprises in its genome at least one copy of a BMR mutation (e.g., bm3, bm3-1, bm3-2) to a second parent corn plant, so as to produce $F_1$ progeny. The first plant can be any BMR corn plant including, for example, BMR corn varieties F2F297, F2F383, F2F488, F2F449, F2F566, F2F610, F2F622, F2F665, F2F633, F2F682, F2F721, F2F700, and F2F797. The second parent corn plant can be any corn plant that is capable of producing viable progeny corn plants (i.e., seeds) when crossed with the first corn plant. The first and second parent corn plants may be of the same corn species (e.g., *Zea mays* (maize)). The methods may further involve selfing the $F_1$ progeny to produce $F_2$ progeny. Methods may further involve one or more generations of backcrossing the $F_1$ or $F_2$ progeny plants to a plant of the same line or genotype as either the first or second parent corn plant. Alternatively, the $F_1$ progeny of the first cross, or any subsequent cross, can be crossed to a third corn plant that is of a different line or genotype than either the first or second plant.

In some embodiments, progeny plants are subjected to a genotype and/or zygosity determination of the disclosure. Once progeny plants have been genotyped, and/or their zygosity has been determined, the skilled artisan may select those progeny plants that have a desired genetic composition. Such selected progeny plants may be used in further crosses, selfing, or cultivation. Methods of introgression of a BMR mutation that are directed according to methods of the disclosure reduce or eliminate the cultivation and/or reproduction of plants that do not have a desired genetic composition, and thereby provide desirable reliability and predictability (through expected Mendelian patterns of inheritance).

The following Examples are provided to illustrate certain particular features and/or embodiments. The following Examples should not be construed to limit the disclosure to the particular features or embodiments described.

EXAMPLES

Example 1

Materials and Methods

Plant and genetic material. Corn leaf samples containing homozygous bm3 alleles and homozygous wild type COMT alleles were provided.

Isolation of total genomic DNA and quantification. Eight leaf discs were punched per sample, and were ground to a fine powder using a Genogrinder® 2000. DNA was extracted with Qiagen DNeasy™ 96-well kit (Valencia, Calif.). Prior to PCR, DNA samples were quantified with Quant-iT™ PicoGreen® Quantification Kit (Invitrogen, Carlsbad, Calif.) using the manufacturer's instructions.

Cloning and sequencing of partial COMT gene. Corn genomic DNA fragments of a partial COMT gene were amplified from twelve bm3 lines and three non-bm3 samples (see Table 1) with oligos BM35_F (5'-TACTCTACTGGCTGCGGCTAGC-3'; SEQ ID NO:1) and BM34_R (5'-TAAC-CTTGATTGTTATTACTCGCACATGG-3'; SEQ ID NO:2) using ABI GeneAmp® PCR System 9700 (Applied Biosystems, Foster City, Calif.) in reactions containing 2.5 units of TaKaRa LA Taq® (Takara Bio Inc., Shiga, Japan), 400 nM dNTP, 200 nM forward (BM35_F) and reverse primer (BM34_R) and 30 ng of genomic DNA. The PCR program began with two minutes of denaturing at 94° C., followed by 30 cycles of 94° C. for 45 seconds, 55° C. for 45 seconds, and 72° C. for two minutes. PCR products were visualized on a 2% E-Gel® (Invitrogen, Carlsbad, Calif.), and then extracted on 0.8% E-Gel® CloneWells™. Purified PCR products were then cloned into pCR4-TOPO® vector (Invitrogen, Carlsbad, Calif.), according to the manufacturer's instruction. Selected colonies were grown overnight in 1× freezer media containing 2.5% LB (10 g tryptone, 10 g NaCl, and 5 g yeast extract for 1 L LB media), 36 mM $K_2HPO_4$, 13 mM $KH_2PO_4$, 1.7 mM sodium citrate, 6.8 mM $(NH_4)_2SO_4$, 4.4% glycerol, 0.4 mM $MgSO_4.7H_2O$, 12.5 µg/mL chloramphenicol (added immediately before use), and 50 ng/ml Kanamycin. Selected colonies were then sent to Cogenics® (Houston, Tex.) for sequencing with T7 and T3 promoter, as well as BM1234R (5'-ATCAGCATCAGCCAGGCAGG-3'; SEQ ID NO:3), which is located within the COMT gene. Sequences were analyzed using Sequencher® 4.8 software. Bm3 mutations were identified by comparing consensus sequences from bm3 lines to wild type COMT samples.

TABLE 1

List of twelve bm3 and three non-bm3 inbred lines used for cloning and sequencing of COMT genes.

| Genotype | Inbred lines |
|---|---|
| bm3 lines | SMM06BM |
| | SLD32BM |
| | SRD02BM |
| | 11084BM |
| | BE1146BMR |
| | IAA18BM |
| | 3633BMR |
| | PIA05BM |
| | PED04BM |
| | LLD44BM |
| | PEA55BM |
| | SMA96BM |
| COMT wild type | SLM07 |
| | 6XN442 |
| | 515Dbm1 |

TaqMan® PCR assay design and validation. Based on the DNA consensus sequences from bm3 lines, primers (BM3_F; SEQ ID NO:4 and BM3_R; SEQ ID NO:5), and probe (BM3_Probe; SEQ ID NO:6) specific to the junction where partial sequences from COMT gene at the 3' end was deleted for identifying the mutant allele; primers (COMT_F and COMT_R) and probe (COMT_probe) within the deleted region for identifying the wild type alleles were designed. Primer Express 3.0 was used for TaqMan® assay design. All primers, and dual labeled probes with FAM or VIC and Minor Groove Binding Non Flourescence Quencher™ I (MGBNFQ) dyes, were synthesized by Applied Biosystems (Foster City, Calif.). All primers and probes were dissolved in 1× Tris-EDTA to 100 µM. TaqMan® genotyping master mix (Applied Biosystems, Foster City, Calif., Catalog #4371355) were used for all PCR reactions.

Real time PCR reactions in 20 µL volume were set up according to Table 2 using 96-well plate on an iCycler® optical system (BioRad, Hercules, Calif.), starting with 15 minutes of denaturing at 95° C., followed by 50 cycles of 92° C. for 15 seconds, and 60° C. for 1 minute. Fluorescence signals were recorded at the end of each cycle.

TABLE 2

PCR mixtures for each biplex reaction with 20 µL final volume.

| Component | Volume (µL) |
|---|---|
| Taqman Genotyping Master Mix (2X, cat# 4371355) | 10 |
| BM3_F (100 µM) | 0.18 |
| BM3_R (100 µM) | 0.18 |
| COMT_F (100 µM) | 0.18 |
| COMT_R (100 µM) | 0.18 |

TABLE 2-continued

PCR mixtures for each biplex reaction with 20 µL final volume.

| Component | Volume (µL) |
|---|---|
| BM3_Probe (100 µM) | 0.04 |
| COMT_Probe (100 µM) | 0.04 |
| DNA (20 to 50 ng/µl) | 1 |
| Water | 8.2 |
| Total volume | 20 |

End-point TaqMan® PCR assays in 10 µl volume were set up according to Table 3 using 384-well plates. ABI GeneAmp® PCR System 9700 (Applied Biosystems, Foster City, Calif.) was used for amplification, starting with 15 minutes of denaturing at 95° C., followed by 30 cycles of 92° C. for 15 seconds, and 60° C. for 1 minute. PCR products were measured by a spectrofluorometer (Tecan GENios™, Männedorf, Switzerland) after an optimal number of cycles, when the reactions were in the early exponential phase with recommended instrument settings (FAM (bm3 mutant): Excitation-485 nm, Emission-535 nm; VIC (wild-type COM7): Excitation-525 nm, Emission-560 nm).

TABLE 3

PCR mixtures for each biplex reaction with 10 µl final volume.

| Component | Volume (µL) |
|---|---|
| Taqman Genotyping Master Mix (2X, cat# 4371355) | 5 |
| BM3_F (100 µM) | 0.09 |
| BM3_R (100 µM) | 0.09 |
| COMT_F (100 µM) | 0.09 |
| COMT_R (100 µM) | 0.09 |
| BM3_Probe (100 µM) | 0.02 |
| COMT_Probe (100 µM) | 0.02 |
| DNA (10 to 20 ng/µl) | 1 |
| water | 3.6 |
| Total volume | 10 |

Data analysis. For real-time PCR, the fluorescence threshold was calculated automatically with its value slightly above the background by iCycler® software. The threshold cycle (Ct value) was determined by the number of cycles needed to generate fluorescence above the established threshold. An allelic discrimination assay was then used to determine genotypes.

Following completion of the endpoint TaqMan® PCR and fluorescence reading, signal over the background of report dye 1 (SOB1) and signal over background of report dye 2 (SOB2) were calculated. A distribution graph between sample numbers and absolute ratios of SOB1/SOB2 in a logarithmic scale were generated. Samples of wild-type, hemizygous, and homozygous plants of similar genotypic background were used as controls. Genotype determinations were made based on the cluster separations.

The raw fluorescence intensity data directly from the plate reader were also analyzed using KLIMS (KBioscience laboratory information management system). Graphs with RFU (relative fluorescence units) of FAM plotted on the x-axis and VIC plotted on the y-axis were generated. Zygosity determinations were made based on the cluster separation in a cluster view.

Example 2

Sequence Analysis of Partial bm3 Mutations of the COMT Gene

Figure 2:
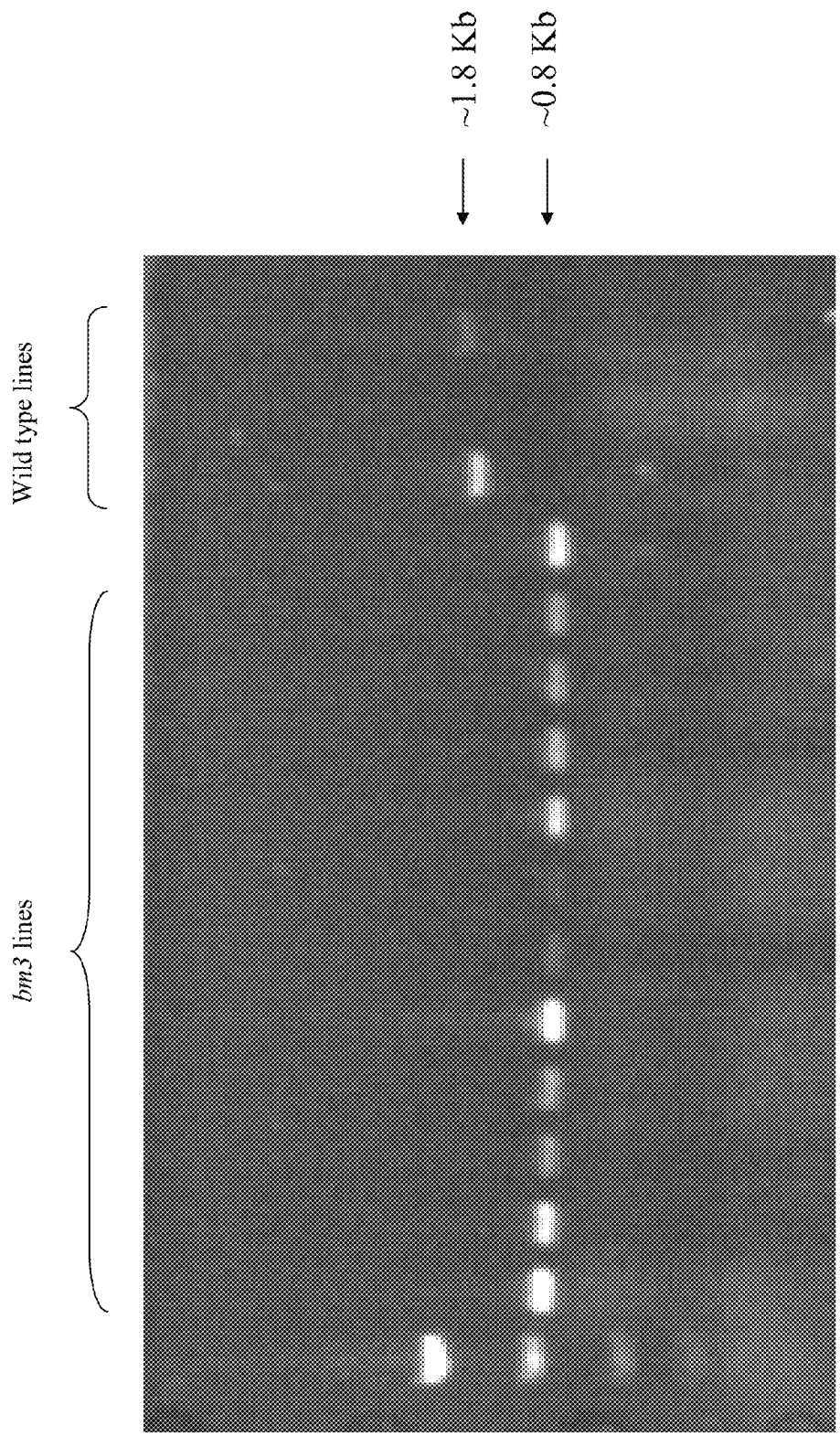
FIG. 2 includes a depiction of the amplification of partial COMT gene sequence from twelve bm3 lines and three non-bm3 lines (wild-type lines). PCR products were visualized on a 2% E-Gel® and then extracted through a 0.8% E-Gel® CloneWell for subsequent cloning into pCR4-TOPO® vector.

To design a gene specific TaqMan® assay for bm3 mutants, precise sequence information was needed. Therefore, two oligonucleotides were designed to amplify partial COMT gene (FIG. 1) from genomic DNA from twelve bm3 and three non-bm3 lines. FIG. 2. These fragments were cloned into pCR4-TOPO® vector, and sent to Cogenics, Inc. for sequencing with T7 and T3 promoter, as well as BM1234R (SEQ ID NO:3). BM1234R is located in the middle of the COMT gene and was used to achieve the full-length sequence information. High quality sequences from nine bm3 lines were analyzed and aligned using Sequencher® 4.8. Consensus sequences from bm3 lines were compared with wild-type samples. Multiple deletion/insertion mutations at the 3' end of the COMT gene were identified. For example, three mutations were confirmed and underlined. FIG. 3.

Figure 4:
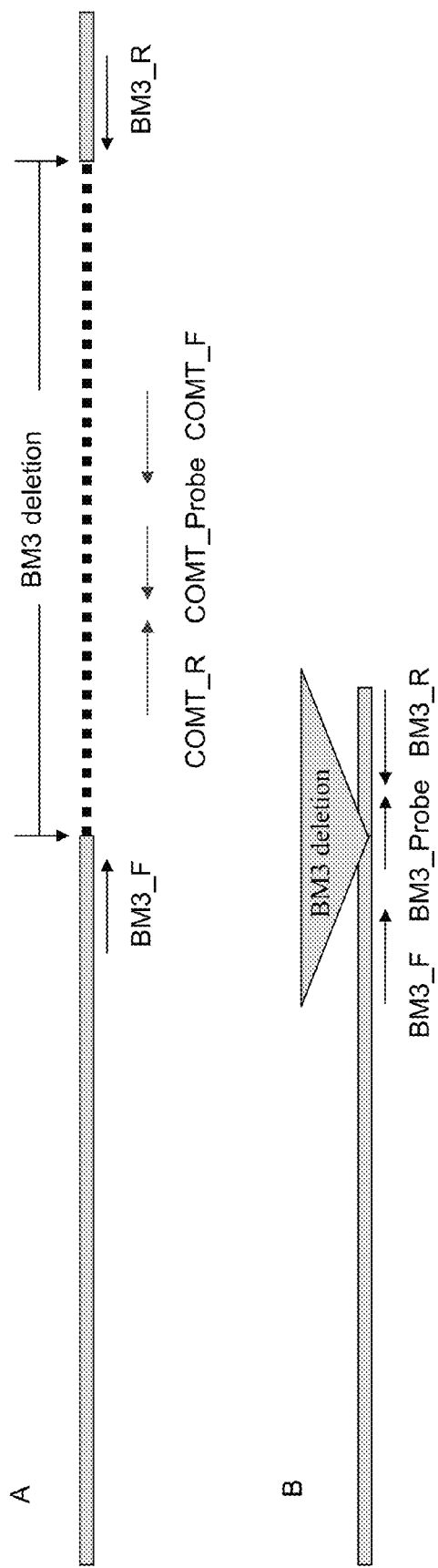
FIG. 4 includes a schematic presentation of COMT gene with primers specific to bm3 mutation and intact COMT gene. (A) COMT gene with dotted lines represents bm3 deletion. COMT gene specific primers are within the deletion site. (B) bm3 mutant gene. bm3 specific oligonucleotides are in the junction where the forward and reverse oligonucleotides flanking the deletion site and the probe span the deleted region.

Gene specific assay design and validation. All the bm3 lines we have tested contain a large deletion mutation at the 3' exon of the COMT gene. This mutation was then used for gene specific TaqMan® assay design. FIG. 4 includes a schematic representation showing the locations of oligonucleotides. Wild-type COMT gene specific primers and probes are located within the 978 bp deletion site. Bm3 specific primers and probes are located in the junction where the forward and reverse oligonucleotides flanking the deletion site and the probe span the deleted region.

Figure 5A:
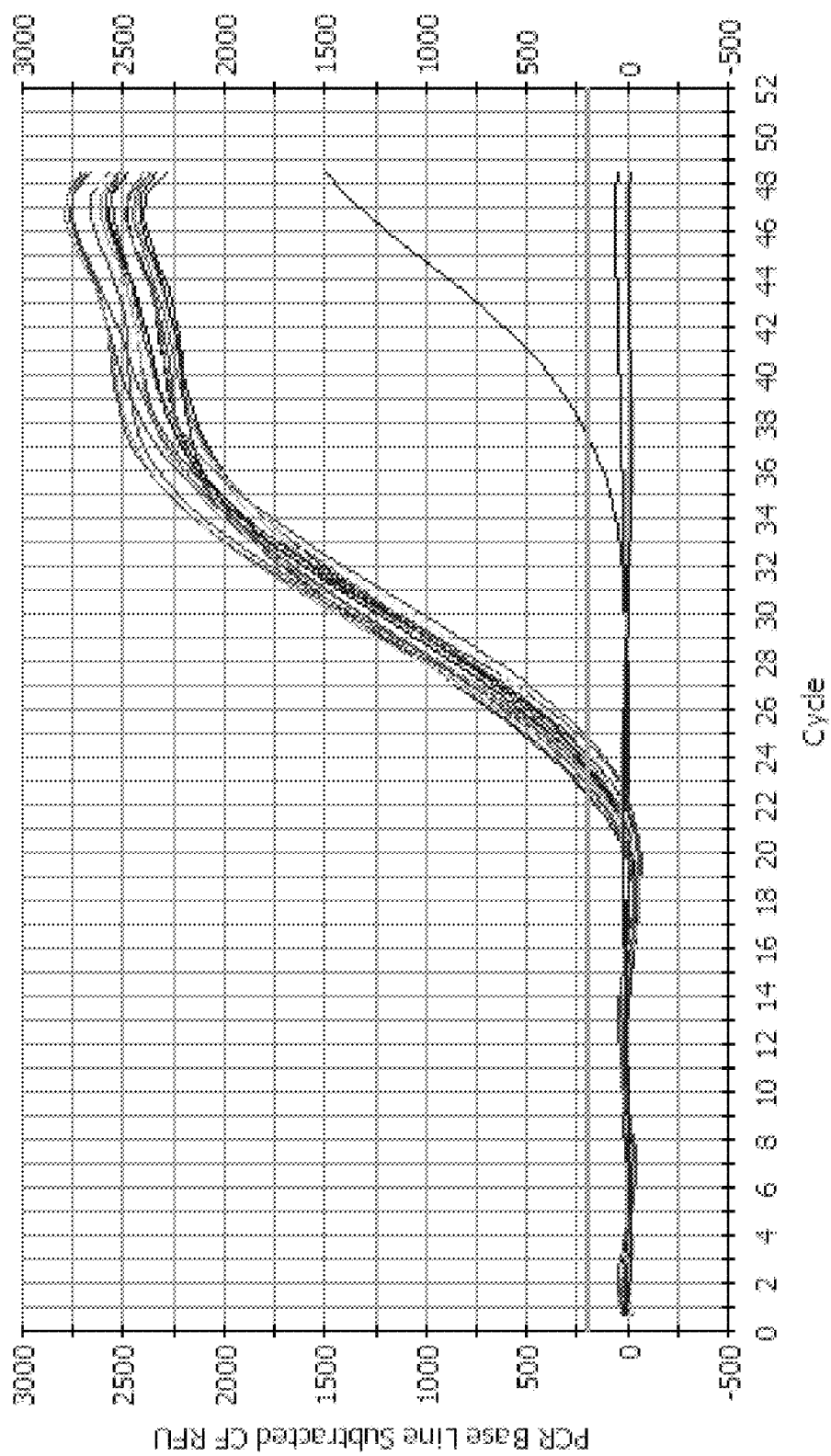
FIGS. 5a and 5b include real-time PCR amplification plots where relative fluorescence units (RFU) are shown for bm3 (a) with FAM and (b) wild-type COMT with VIC (replaced with Hex because of the limitation of the real time PCR machine). Exponential amplification phase was observed from cycle 22 to 36 for both bm3 and wild-type COMT genes.
Figure 5B:
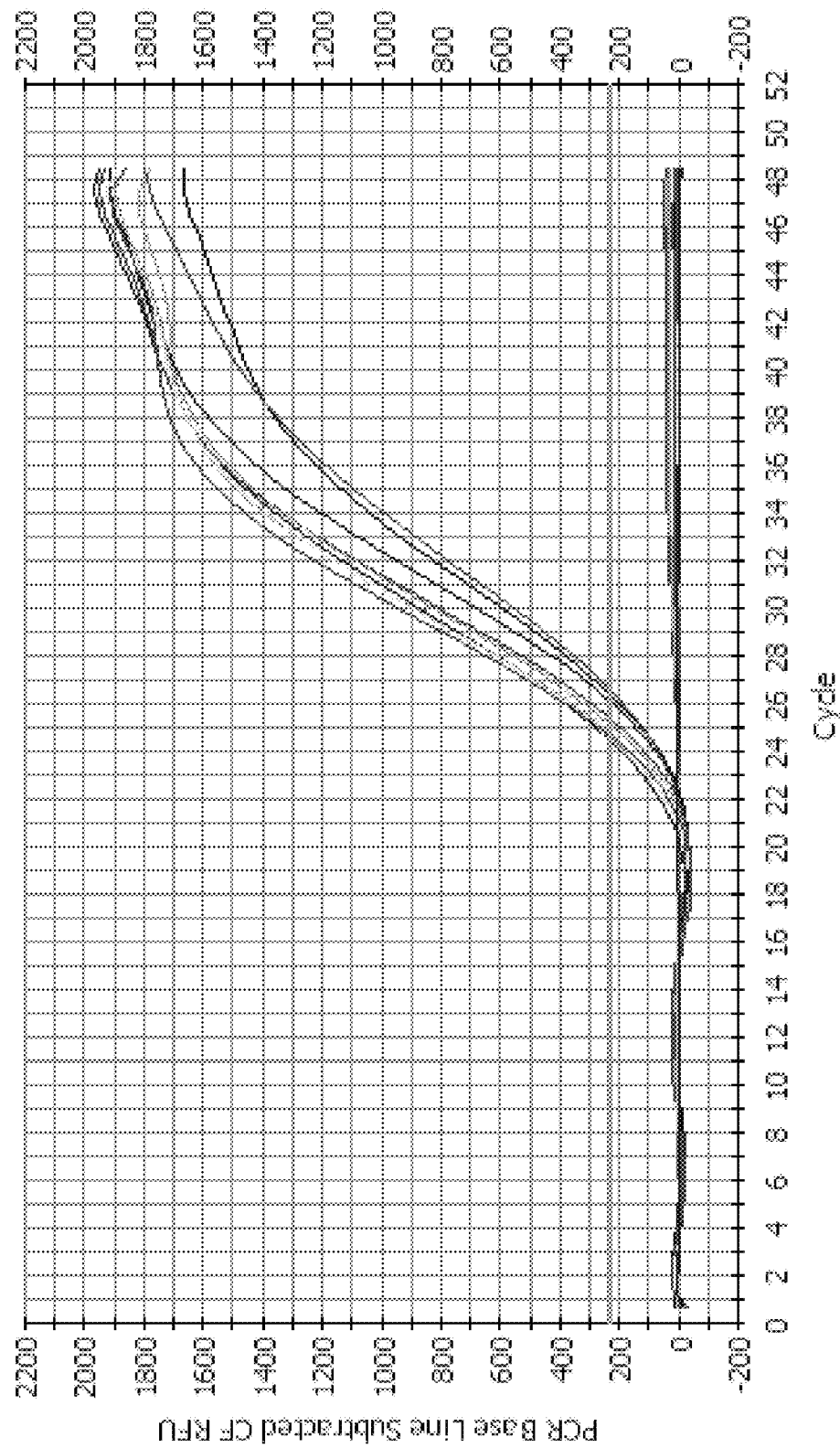
Figure 6:
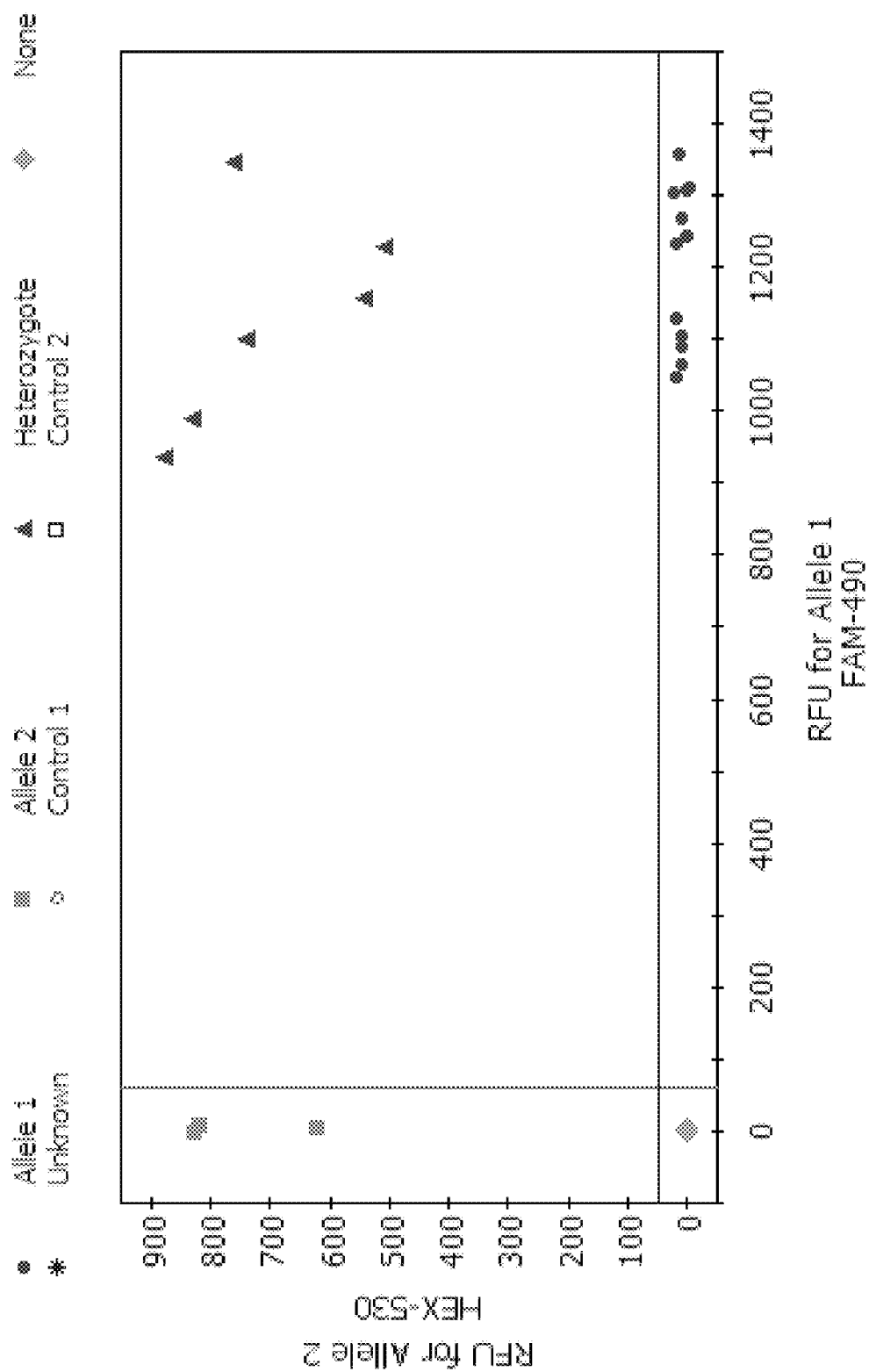
FIG. 6 includes genotype determinations made using an allelic discrimination assay based on relative fluorescence units of FAM as allele 1 (homozygous bm3) and VIC (replaced with Hex because of the limitation of the machine) as allele 2 (homozygous wild-type COMT) at cycle 30.

The twelve known bm3 lines and the three non-bm3 lines were used to test the gene specific TaqMan® assay. Six hemizygous samples were made by combining equal amounts of DNA from bm3 lines with non-bm3 lines. Real time PCR was used to test the efficiency of the assay. Oligonucleotides specific to the bm3 mutants and to the corresponding wild-type sequences were combined in the same assay. FAM was used to monitor the amplicon of bm3, and VIC was used to monitor the amplicon for wild-type COMT. Exponential amplification phase was observed from cycle 22 to 36 for both bm3 and wild-type COMT genes. See FIGS. 5a and 5b. Correct genotype determinations were generated using an allelic discrimination assay based on FAM as allele 1 and VIC as allele 2 at cycle 30. FIG. 6.

Validation of end-point TaqMan® zygosity analysis. One 96-well plate of DNA samples containing bm3 populations segregating as homozygous, hemizygous, and null (wild-type) was used to test and validate an end-point TaqMan® PCR assay. One advantage of end-point TaqMan® PCR is the ease of use. End-point TaqMan® PCR does not require a more expensive real-time PCR machine. Any regular PCR machine fit for 96- or 384-well plates, and a plate reader capable of reading the relevant fluorescent signal are sufficient to carry out the assay.

Figure 7:
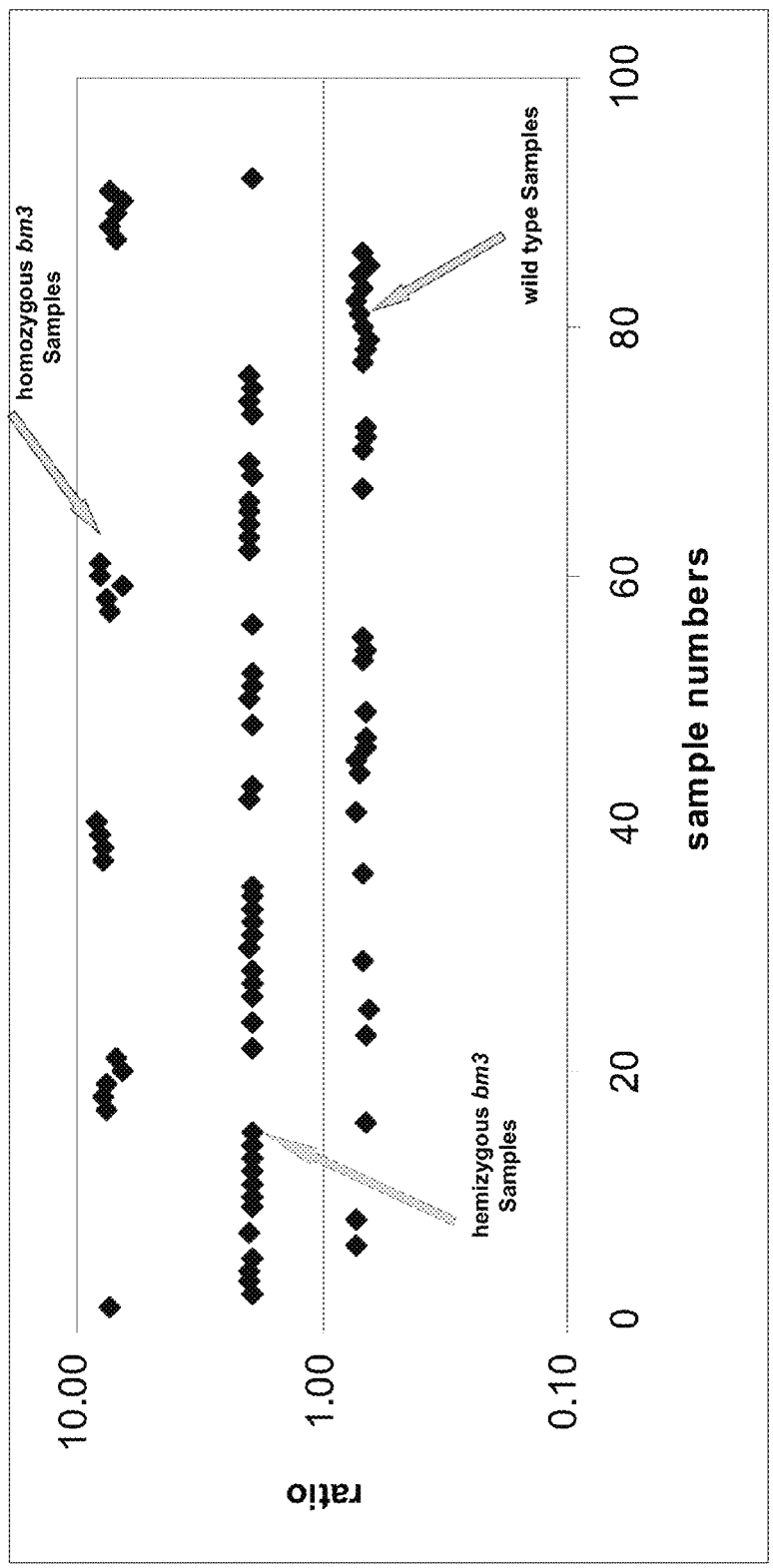
FIG. 7 includes bm3 zygosity determinations made with an end-point TaqMan® assay. On completion of PCR and fluorescence readings, a distribution graph was generated as described below: SOB1=Signal over the background of FAM (sample signal over average of background signal at 535 nm), SOB2=Signal over background of VIC (sample signal over average of background signal at 560 nm). Genotype determinations were made with SOB1/SOB2<1 for wild-type, 1<SOB1/SOB2<5 for hemizygotes, and SOB1/SOB2>5 for homozygotes with a logarithmic scale.

Based on the results from real-time PCR, 30 cycles of PCR reaction can efficiently separate the bm3 genes from the wild-type COMT genes. The PCR reaction was terminated at cycle 30. Following completion of the TaqMan® PCR and fluorescence reading, fluorescence signals of FAM (bm3) over background ($H_2O$), as signal over background 1 (SOB1); and VIC (wild-type COMT) over background 2 (SOB2) were calculated. A distribution graph was generated using SOB1/SOB2 in a logarithmic scale. FIG. 7. Wild-type, hemizygous, and homozygous controls of similar genotypic background served as negative and positive controls. In a segregating population, three clusters of data points were obtained, allowing the cut-off points to be visually determined. For the example in FIG. 7, three clusters of data points were clearly visible. The data points for wild-type are less than 1, those for hemizygous samples range from 1 to 5, and those for homozygous are above 5.

Figure 8:
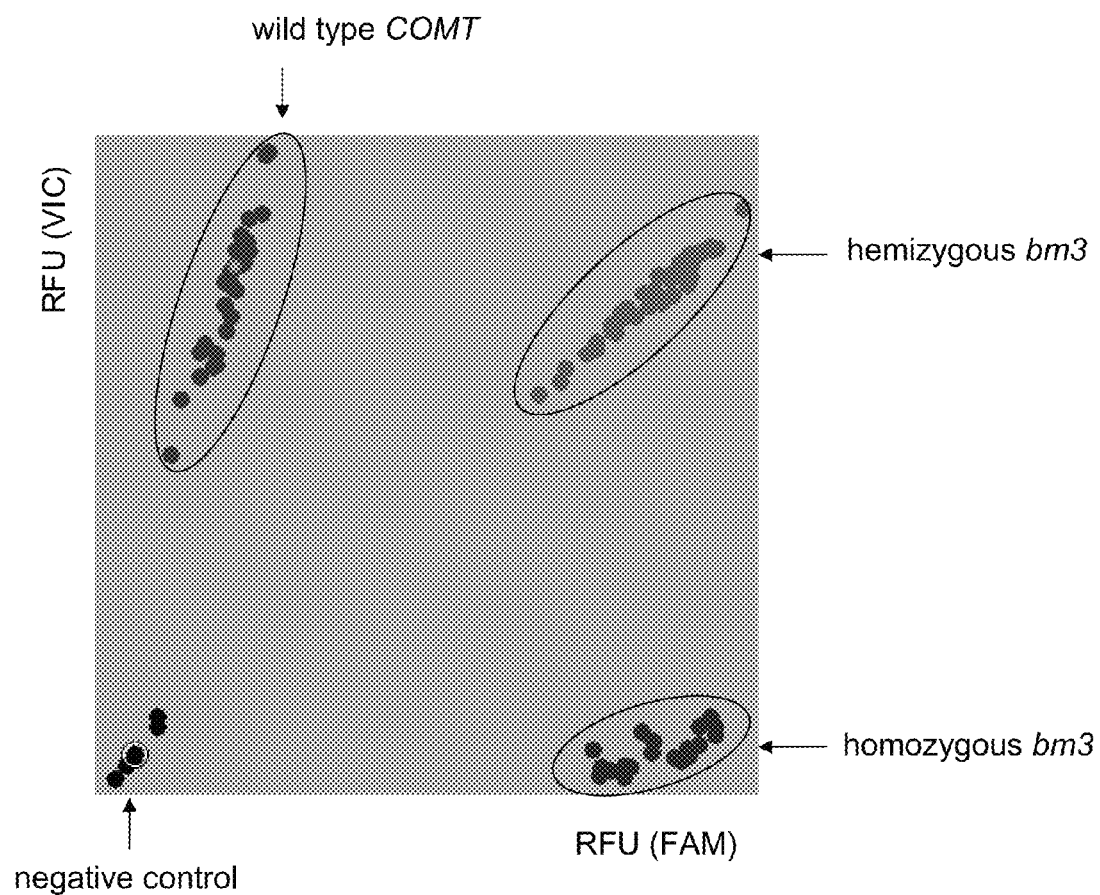
FIG. 8 includes bm3 zygosity determinations made with an end-point TaqMan® assay. The raw fluorescence intensity data directly from the plate reader was analyzed in KLIMS (KBioscience laboratory information management system). A graph with RFU (relative fluorescence units) of FAM plotted on the x-axis and VIC plotted on the y-axis was generated. Zygosity determinations were made based on the cluster separation in a cluster view.

The raw fluorescence intensity data directly from the plate reader was also analyzed in KLIMS (KBioscience laboratory information management system). A graph with RFU (relative fluorescence unit) of FAM plotted on the x-axis, and VIC plotted on the y-axis was generated. Zygosity determinations were made based on the cluster separation in a cluster view. FIG. 8. Since FAM was used to monitor the amplification of bm3, and VIC was used to monitor the amplification of wild-type COMT, samples with strong signals of FAM, and little or no VIC signal, are homozygous bm3; samples with strong signals of VIC, and little or no FAM, are wild-type COMT (nulls); and samples with strong signals of both FAM and VIC are hemizygous.

Genotype and zygosity determinations from this bm3 gene specific end-point TaqMan® PCR assay matched 100% with phenotypic data collected in the field. This assay provides an easy and accurate way to characterize the bm3 zygosity status in a high-throughput manner.

Example 3

Introgression of bm3 Mutation

The zygosity of a corn plant with respect to the bm3 mutation is determined as described, supra. It is determined that the corn plant is homozygous for the bm3 mutation. The plant is crossed through conventional plant breeding with a corn plant known to be homozygous for the wild-type COMT gene, and a corn plant homozygous for the bm3 mutation. $F_1$ progeny of the cross are produced. $F_1$ progeny of the cross are then selfed to produce $F_2$ progeny. Samples of genomic DNA of the $F_2$ progeny are prepared and the zygosity of the $F_2$ progeny plants are determined as described, supra.

$F_2$ progeny plants are selected that are homozygous for the bm3 mutation. The selected progeny are then assayed for low lignin content, and those progeny that exhibit desirably low lignin levels are further reproduced by crossing and selfing, and the resulting progeny are cultivated.

While the present invention has been described herein with respect to certain preferred embodiments, those of ordinary skill in the art will recognize and appreciate that it is not so limited. Rather, many additions, deletions, and modifications to the preferred embodiments may be made without departing from the scope of the invention as hereinafter claimed. In addition, features from one embodiment may be combined with features of another embodiment while still being encompassed within the scope of the invention as contemplated by the inventors.

What is claimed is:

1. A method for determining the zygosity and/or presence/absence of an allele using corn plant tissue, the method comprising:

obtaining a sample of isolated genomic DNA from the corn plant tissue;

contacting the genomic DNA with at least two nucleic acid molecules capable of hybridizing to SEQ ID NO:10 under high stringency conditions, and with at least two nucleic acid molecules capable of hybridizing to SEQ ID NO:11 under high stringency conditions;

amplifying the nucleotide sequence of the genomic DNA between nucleotide sequences of the genomic DNA that hybridize to the nucleic acid molecules capable of hybridizing to SEQ id NO:10 under high stringency conditions;

amplifying the nucleotide sequence of the genomic DNA between nucleotide sequences of the genomic DNA that hybridize to the nucleic acid molecules capable of hybridizing to SEQ ID NO:11 under high stringency conditions;

including in the amplifying reaction at least one first polynucleotide capable of hybridizing to SEQ ID NO:10 under high stringency conditions that is not capable of hybridizing to SEQ ID NO:11 under high stringency conditions, wherein the first polynucleotide is labeled with a first reporter, and including in the amplifying reaction at least one second polynucleotide capable of hybridizing to SEQ ID NO:11 under high stringency conditions that is not capable of hybridizing to SEQ ID NO:10 under high stringency conditions, wherein flee second polynucleotide is labeled with a second reporter; and detecting the levels of the first and second reporter that are hybridized to the genomic DNA, thereby determining zygosity of a bm3 mutation in the isolated genomic DNA.

2. The method of claim 1, wherein the first reporter and the second reporter are fluorescent dyes with distinguishable excitation/emission spectra.

3. The method of claim 2, wherein the first reporter is FAM, and the second reporter is VIC.

4. The method of claim 1, wherein the at least one nucleic acid molecule comprising a nucleotide sequence capable of hybridizing to SEQ ID NO:10 is between 10 and 35 nucleotides in length.

5. The method of claim 4, wherein the at least one nucleic acid molecule comprising a nucleotide sequence capable of hybridizing to SEQ ID NO:10 is between 15 and 30 nucleotides in length.

6. The method of claim 4, wherein one of the at least one nucleic acid molecules comprising a nucleotide sequence capable of hybridizing to SEQ ID NO:10 is at least 95% identical to between 10 and 35 contiguous nucleotides of SEQ ID NO:10.

7. The method of claim 6, wherein the at least one nucleic acid molecule comprising a nucleotide sequence capable of hybridizing to SEQ ID NO:10 is selected from the group consisting of SEQ ID NO:4, SEQ ID NO:5, and SEQ ID NO:6.

8. The method of claim 1, wherein at least one nucleic acid molecule comprising a nucleotide sequence capable of hybridizing to SEQ ID NO:10 under high stringency conditions is labeled with FAM, and at least one nucleic acid molecule capable of hybridizing to SEQ ID NO:11 under high stringency conditions is labeled with VIC.

9. The method of claim 1, wherein amplifying the nucleotide sequence comprises amplifying in a PCR reaction.

* * * * *

SEQUENCE LISTING

<160> NUMBER OF SEQ ID NOS: 11

<210> SEQ ID NO 1
<211> LENGTH: 22
<212> TYPE: DNA

```
<213> ORGANISM: Artificial Sequence
<220> FEATURE:
<223> OTHER INFORMATION: forward primer sequence BM35_F

<400> SEQUENCE: 1
tactctactg gctgcggcta gc                                          22

<210> SEQ ID NO 2
<211> LENGTH: 29
<212> TYPE: DNA
<213> ORGANISM: Artificial Sequence
<220> FEATURE:
<223> OTHER INFORMATION: Reverse primer BM35_R

<400> SEQUENCE: 2
taaccttgat tgttattact cgcacatgg                                   29

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide sequence BM1234R

<400> SEQUENCE: 3
atcagcatca gccaggcagg                                             20

<210> SEQ ID NO 4
<211> LENGTH: 25
<212> TYPE: DNA
<213> ORGANISM: Artificial Sequence
<220> FEATURE:
<223> OTHER INFORMATION: Forward primer BM3_F

<400> SEQUENCE: 4
aaaaagaacg aggttgcaaa agata                                       25

<210> SEQ ID NO 5
<211> LENGTH: 23
<212> TYPE: DNA
<213> ORGANISM: Artificial Sequence
<220> FEATURE:
<223> OTHER INFORMATION: Reverse primer BM3_R

<400> SEQUENCE: 5
ttagaatcca cgacatgcaa gag                                         23

<210> SEQ ID NO 6
<211> LENGTH: 18
<212> TYPE: DNA
<213> ORGANISM: Artificial Sequence
<220> FEATURE:
<223> OTHER INFORMATION: bm3 probe BM3_Probe

<400> SEQUENCE: 6
acaaaccaaa ggatgtcg                                               18

<210> SEQ ID NO 7
<211> LENGTH: 19
<212> TYPE: DNA
<213> ORGANISM: Artificial Sequence
<220> FEATURE:
<223> OTHER INFORMATION: Forward primer COMT_F

<400> SEQUENCE: 7
cgcactcgac gacgatgac                                              19
```

```
<210> SEQ ID NO 8
<211> LENGTH: 21
<212> TYPE: DNA
<213> ORGANISM: Artificial Sequence
<220> FEATURE:
<223> OTHER INFORMATION: Reverse primer COMT_R

<400> SEQUENCE: 8
cacgctgctc aagaactgct a                                              21

<210> SEQ ID NO 9
<211> LENGTH: 16
<212> TYPE: DNA
<213> ORGANISM: Artificial Sequence
<220> FEATURE:
<223> OTHER INFORMATION: COMT probe COMT_Probe

<400> SEQUENCE: 9
cattttccgg cagcgc                                                    16

<210> SEQ ID NO 10
<211> LENGTH: 825
<212> TYPE: DNA
<213> ORGANISM: Zea mays

<400> SEQUENCE: 10
tactggctgc ggctagcaca aggctggaaa tagttattat ctacgatata atatttccct     60
agaacaaaaa aagttttttt ataaaaagca agaaagaaag aaggaaagaa agtgagtgac    120
ttcaagtttt tcctaaaaaa aaagttagga gtgggatgga aaagtcagca aggaccactt    180
gtttgttgtc cactatccat ccagtgggtg agacttttt gcgagacgga gcactatatt    240
attggccgac tccttttct gtatccgcaa acggcagcc gtcgatcgcc ggacggatcg    300
acggctcaca tgagtgtcga gtccaattcc aaccacgagg ctggaagga aaccatccg    360 tgctggtctg acttttttgc caaactccat tcagccattc gccgactgaa ggtgaatctt    420
cagacagcca gattggttgg tgtctagtgt gtgcgaagat ggcgtagaaa agactgagag    480
acagttggct cacacagaca attgacaact gactatagta tctgcctgcc tggctgatgc    540
tgatagagat ggggactctt gtcctgctgt ctgttcttgt ataaatctcc gttgtcaaat    600
atttatcgtc cgattattta tttytaaact aaacaacgac aaataaaaaa gaacgaggtt    660
gcaaaagata gatacaaacc aaaggatgtc gagctcttgc atgtcgtgga ttctaaattc    720
ttcttctgcg tcgaattgtc tctgccatgt gcgagtaata acaatcaagg ttatacttac    780
catacaatta catggtggtt taattgctct ctttaatttt ggtga                    825

<210> SEQ ID NO 11
<211> LENGTH: 2512
<212> TYPE: DNA
<213> ORGANISM: Zea mays

<400> SEQUENCE: 11
ggtgagccgt ccggcccaat aaaacccct cgcaccacct cgtccctctt cgtcgcatcg     60
cacgccatca gcagctagcg cgctcctcga gcccagcaga gaaaggccgg cagcgctaat    120
cgtaatagcc atgggctcca ccgccggcga cgtggccgcg gtggtggacg aggaggcgtg    180
catgtacgcg atgcagctgg cgtcgtcgtc catcctgccc atgacgctga aaacgcccat    240
cgagctgggc ctgctggagg tgctgcagaa ggaggccggc ggcggcaagg cggcgctggc    300
```

```
gcccgaggag gtggtggcgc ggatgcccgc ggcgcccagc gaccccgccg ccgccgcggc      360
catggtggac cgcatgctcc gcctgctcgc ctcctacgac gtcgtccggt gccagatgga      420
ggaccgggac ggccggtacg agcgccgcta ctccgccgcg cccgtctgca agtggctcac      480
ccccaacgag gacggcgtgt ccatggccgc cctcgcgctc atgaaccagg acaaggtcct      540
catggagagc tggtgagtag tagccgcatc gcatcaacca ccttctacct atctatatcc      600
atcacttgtt gctgctggcg tgcgcggcat gcatgatgac gagctcgctc atcattggtg      660
ctactagtga tttatttcgt ccagtaaaat taattaaggt gcgctgctac tctactggct      720
gcggctagca caaggctgga aatagttgtt acttgttata cacgatataa tatttctcta      780
gaacaaaaaa gattttttt ttataaaag caagcaagaa agaaagtgag tgacttcatg       840
tttttcctaa aaaaagtta ggagtgggat ggaaaagtca gcaaggacca cttgtttgtt       900
gtccactatc catccagtgg gtgagacttt tttgcgagac ggagcactat attattggcc      960
gagtcccttt tctgtatccg caaaacggca gccgtcgatc gccggacgga tcgcacggcg     1020
acactgagtg tcgagtccaa ttccaaccac gagggctgga aggaaagcca tccgtgctgg     1080
tctggacttt ttgccaaact ccattcagac gttcgccgac tgaaggtgaa tcttcagaca     1140
cagccagatt gtttggtgtc tgcgaagatg gcgtagaaaa gaccaagaga cagttggctc     1200
acacagacaa gtgacaactg actatagtat ctgcctgcct ggctgatgct gatagagata     1260
gactcttgcc ctgtctgttc cttgtacaaa cgtggacaaa cattagtagc agttttcttt     1320
gatctacaaa aagtactacc tcagttttta aatatttatc ggctgttagt ttatttttga     1380
acttaaacga ctggttgcaa aagatagata gatacaaacg aaaggatgtc gtcgctgtgc     1440
gctgatctga tcactgccac tctgccaggt actatctcaa ggacgcggtg ctggacggcg     1500
gcatcccgtt caacaaggcg tacgggatga cggcgttcga gtaccacggc acggacgcgc     1560
gcttcaaccg cgtgttcaac gagggcatga agaaccactc ggtgatcatc accaagaagc     1620
tgctggactt ctacacgggc ttcgagggcg tgtcgacgct ggtggacgtg ggcggcggcg     1680
tgggcgccac gctgcacgcc atcacgtccc gccacccgca catctccggg gtcaacttcg     1740
acctgccgca cgtcatctcc gaggcgccgc cgttccccgg cgtgcgccac gtgggcgggg     1800
acatgttcgc gtccgtgccc gccggcgacg ccatcctcat gaagtggatc ctccacgact     1860
ggagcgacgc gcactgcgcc acgctgctca agaactgcta cgacgcgctg ccggaaaatg     1920
gcaaggtcat cgtcgtcgag tgcgtgctgc cggtcaacac ggaggccacc cccaaggcgc     1980
agggcgtgtt ccacgtcgac atgatcatgc tcgcgcacaa ccccggcggc aaggagcggt     2040
acgagcgcga gttccgcgag ctcgccaagg gcgccggctt ctccgggttc aaggccacct     2100
acatctacgc caacgcctgg gccatcgagt tcatcaagtg aatacggcta ccaccgtcgc     2160
cgcgatgaga tgcatggctg ccacatgcat gcttgcttgc ttggtcctcg tatcgtacgt     2220
cgccgtcgtc gtcttcttct ggttgcgctg ctaccttgct gctctcgccc tcgcgtatgc     2280
atgtactttt gcttaatttt ctttcttcat atcatgcact ctggctggcc tagactgccc     2340
ccgatccatg gtggccatgt cttcggtacg tcttgtcgag tcttgcatg tcgtggattc      2400 taaattcttc ttctgcgtcg aattgtctct gccatgtgcg agtaataaca atcaaggtta     2460
tacttaccat acaattacat ggtggtttaa ttgctctctt ttaatttggt ga             2512
```